United States Patent
Suzuki

(10) Patent No.: US 9,207,216 B2
(45) Date of Patent: Dec. 8, 2015

(54) ULTRASONIC SENSOR HAVING TRASMITTING AND RECEIVING HORNS

(71) Applicant: RISO KAGAKU CORPORATION, Tokyo (JP)

(72) Inventor: Masao Suzuki, Ibaraki-ken (JP)

(73) Assignee: RISO KAGAKU CORPORATION, Tokyo (JP)

( * ) Notice: Subject to any disclaimer, the term of this patent is extended or adjusted under 35 U.S.C. 154(b) by 564 days.

(21) Appl. No.: 13/654,994

(22) Filed: Oct. 18, 2012

(65) Prior Publication Data

US 2013/0098157 A1    Apr. 25, 2013

(30) Foreign Application Priority Data

Oct. 21, 2011    (JP) .................. 2011-231587

(51) Int. Cl.
| | |
|---|---|
| G01N 29/14 | (2006.01) |
| G01N 29/24 | (2006.01) |
| G01N 29/07 | (2006.01) |
| G01C 3/06 | (2006.01) |
| G01S 7/521 | (2006.01) |
| G10K 11/00 | (2006.01) |
| G01S 15/10 | (2006.01) |

(52) U.S. Cl.
CPC .................. *G01N 29/07* (2013.01); *G01C 3/06* (2013.01); *G01N 29/14* (2013.01); *G01N 29/24* (2013.01); *G01S 7/521* (2013.01); *G10K 11/00* (2013.01); *G01S 15/10* (2013.01)

(58) Field of Classification Search
CPC ....... G01S 15/872; G01S 7/521; G01S 7/527; G01K 11/28; G01K 11/025; G01K 11/002; G01K 11/004; G01N 29/14; G01N 29/07; G01N 29/24

USPC .................. 73/596–600, 602, 627–628, 649; 381/340, 342; 181/152, 159, 177, 181/187–188

See application file for complete search history.

(56) References Cited

U.S. PATENT DOCUMENTS

| | | | | |
|---|---|---|---|---|
| 4,104,610 | A | * | 8/1978 | Inoue et al. ..................... 367/93 |
| 4,260,928 | A | * | 4/1981 | Salem ........................... 310/335 |
| 4,358,835 | A | * | 11/1982 | Fage .................................. 367/87 |
| 4,739,860 | A | * | 4/1988 | Kobayashi et al. ........... 181/123 |
| 5,075,863 | A | * | 12/1991 | Nagamune et al. ........... 702/159 |
| 8,452,038 | B2 | * | 5/2013 | Buccafusca et al. .......... 381/340 |
| 2003/0154792 | A1 | * | 8/2003 | Katayama ....................... 73/602 |
| 2006/0043843 | A1 | * | 3/2006 | Sugiura et al. ................ 310/348 |
| 2010/0109481 | A1 | * | 5/2010 | Buccafusca ................... 310/335 |

FOREIGN PATENT DOCUMENTS

| | | |
|---|---|---|
| JP | 63-025578 A | 2/1988 |
| JP | 11-218572 A | 8/1999 |

* cited by examiner

*Primary Examiner* — Helen Kwok
(74) *Attorney, Agent, or Firm* — Greenblum & Bernstein, P.L.C.

(57) ABSTRACT

As a transmitting horn or a receiving horn attached to a transmission element or a reception element of an ultrasonic sensor, a horn enclosure with two acoustic horn bodies having a dimensional difference $\Delta Lh$ of a quarter $\lambda/4$ of the wavelength $\lambda$ of an ultrasonic wave U in the propagation direction X of the ultrasonic wave U or a reflection wave R is used. Then, the amplitude of a diffraction wave A1 and the amplitude of a diffraction wave A2 in opposite phase between a transmission side and a reception side are caused to match with each other so as to cancel out both the diffraction waves A1, A2 in a common sound space of the horn enclosure, which is not partitioned for each acoustic horn body by a screen, on a front of the reception element.

3 Claims, 9 Drawing Sheets

WAVE A2: DIFFRACTION WAVE
WAVE B: REFLECTION WAVE
WAVE A1: DIFFRACTION WAVE

WAVE B: REFLECTION WAVE

FIG. 10A  FIG. 10B  FIG. 10C  FIG. 10D
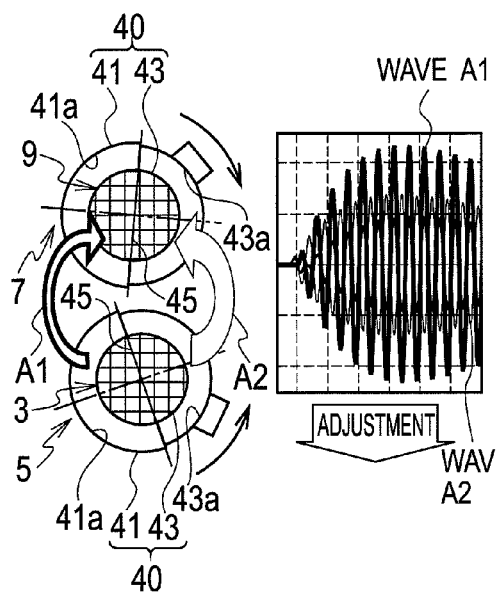
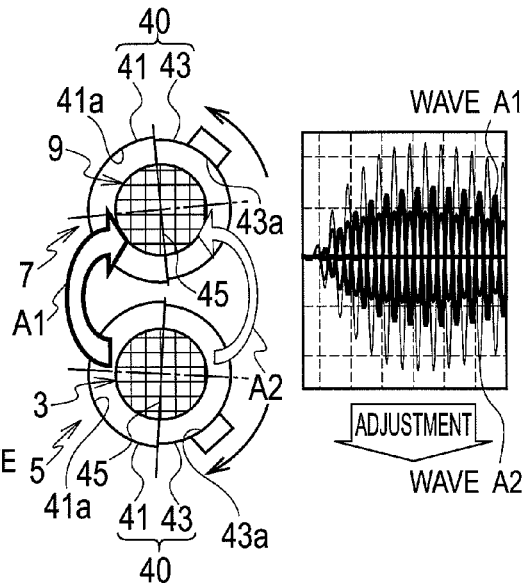
FIG. 10E
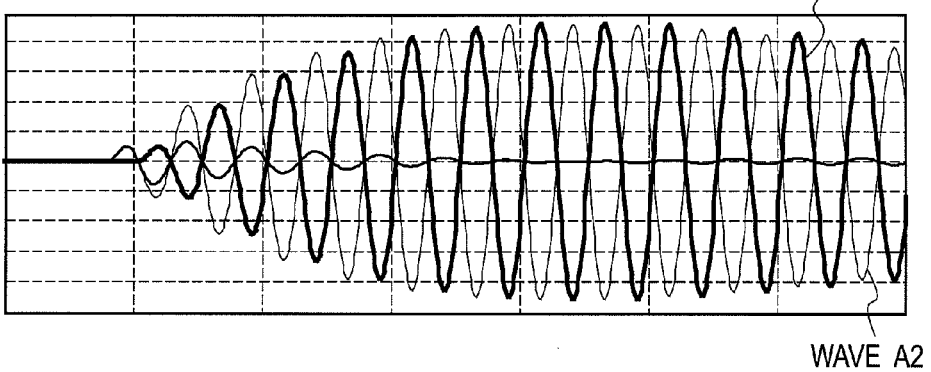

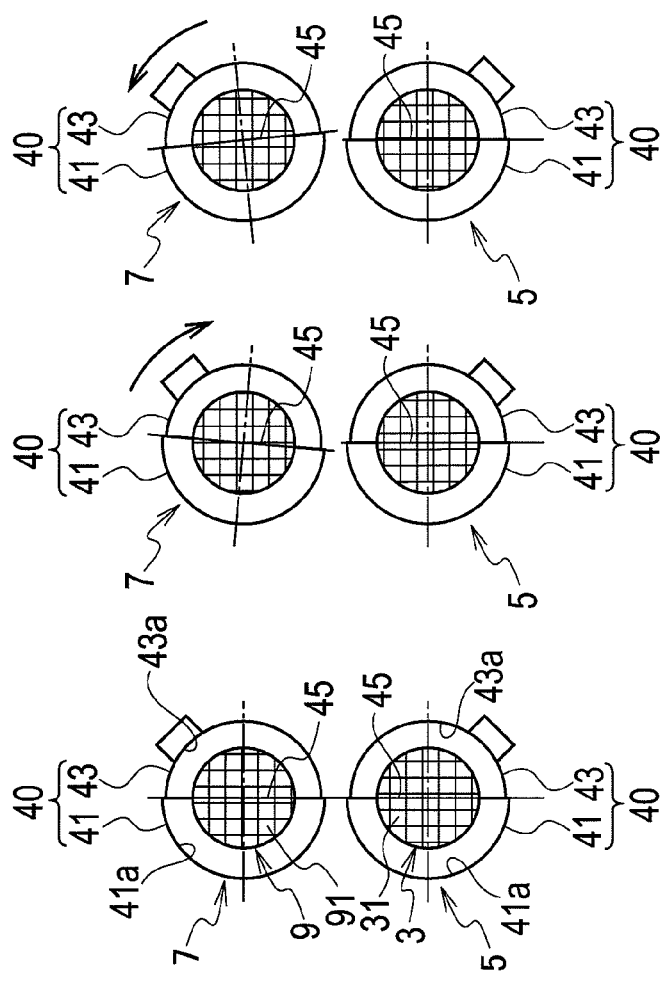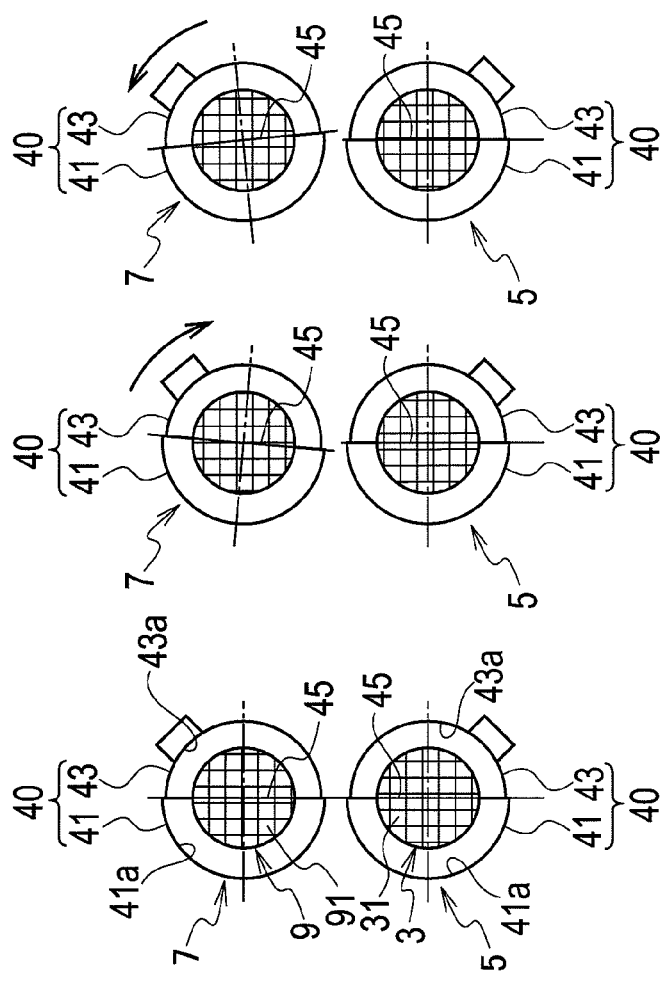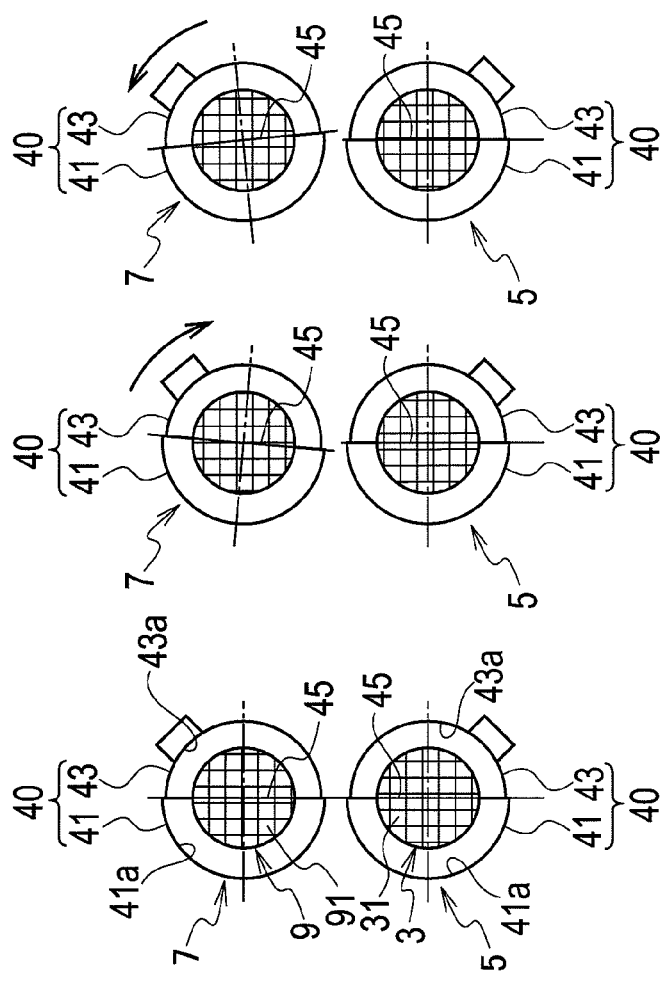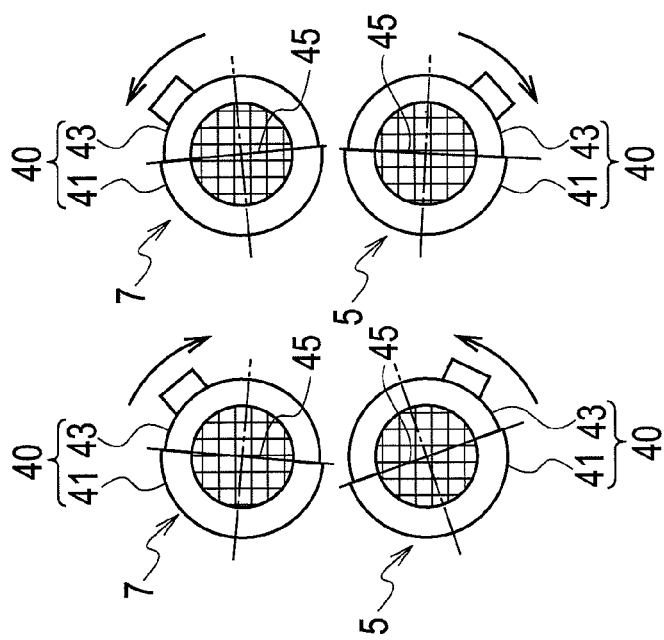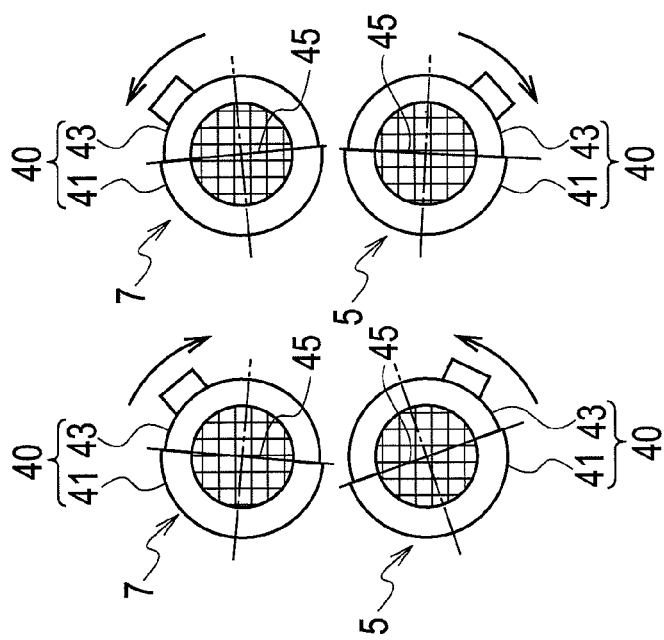

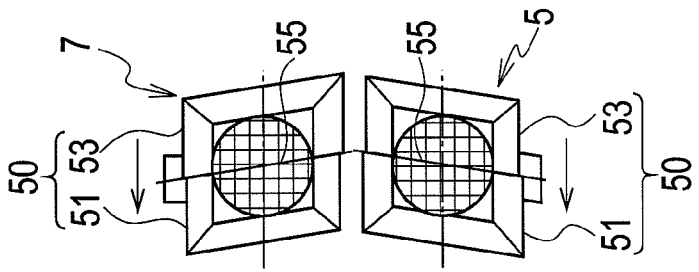
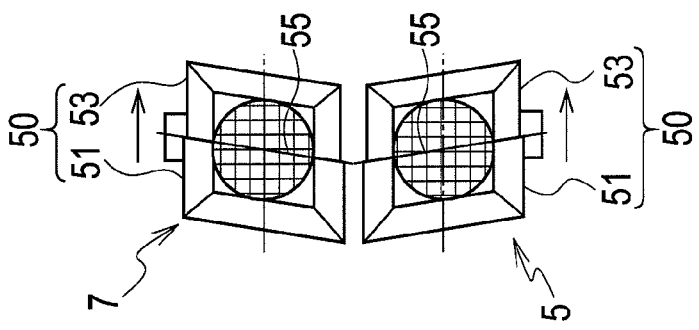
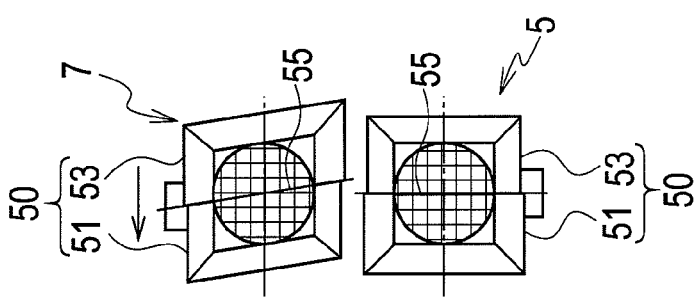
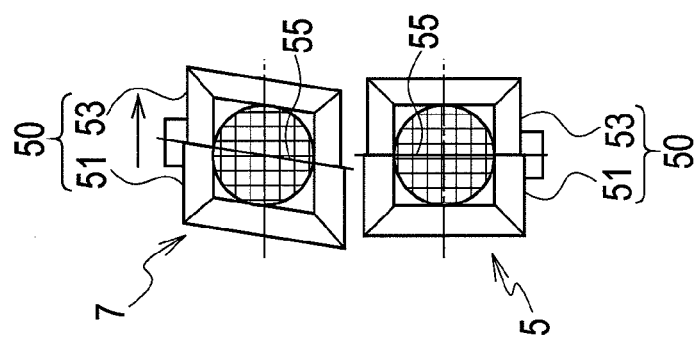
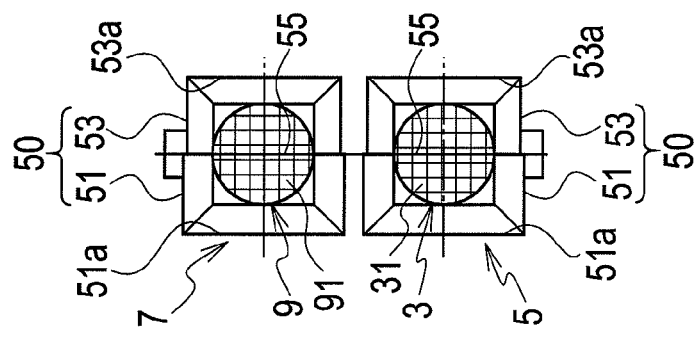

ULTRASONIC SENSOR HAVING TRASMITTING AND RECEIVING HORNS

BACKGROUND OF THE INVENTION

1. Technical Field

The present invention relates to ultrasonic sensors that measure a distance to an object to be detected and the like by transmitting/receiving an ultrasonic wave.

2. Background Arts

The ultrasonic sensor is widely used for applications, such as in measuring a distance to an object to be detected and in detecting the presence of an object to be detected, as with a photosensor and the like. In particular, the ultrasonic sensor is used for the detection of an object to be detected, which a photosensor is not good at detecting, such as the detection of a transparent or semi-transparent film, such as an ultralight paper or a master for a stencil printing plate, the detection of the position of a paper, both sides of which are printed in black, or the detection of the liquid level of ink or the like, in the field of printing, for example.

In the ultrasonic sensor, an ultrasonic wave is transmitted toward an object to be detected, via a transmitting horn from a transmission element transmitting the ultrasonic wave, and a reflection wave from the object to be detected is received by a reception element via a receiving horn. At this time, because the transmitting horn and the receiving horn are arranged side by side each facing to the same direction, a diffraction wave generated at an edge of an opening of the transmitting horn may be further diffracted at an edge of an opening of the receiving horn and received by the reception element, thereby reducing the detection accuracy of the object to be detected.

Then, as the countermeasure for the diffraction wave, there have been already proposed a method of arranging a sound absorbing member between the opening portions of both horns (Japanese Patent Application Laid-Open No. 63-25578), and a method of causing the diffraction wave to be diffracted into grooves provided around both openings to serve as a standing wave (Japanese Patent Application Laid-Open No. 11-218572).

SUMMARY OF THE INVENTION

However, in the two conventional arts described above, a spacing enough to be able to arrange the sound absorbing member or the groove between the openings of the both horns must be provided therebetween, and therefore as compared with the case where the both horns are adjoined, the shortest detection range at which a reflection wave from an object to be detected can be received by a receiving horn or a reception element will increase.

The present invention has been made in view of the above-described circumstances, and provides an ultrasonic sensor capable of suppressing a reduction in the detection accuracy due to the influence of a diffraction wave without spacing apart both the transmitting horn and the receiving horn.

In order to achieve the above-described purpose, an ultrasonic sensor according to one embodiment of the present invention includes: a transmitting horn transmitting an ultrasonic wave generated by a transmission element and a receiving horn causing a reception element to receive a reflection wave from an object to be detected of the transmitted ultrasonic wave, in which the transmitting horn and the receiving horn share a common horn enclosure, in which the horn enclosure has two acoustic horn bodies, positions of openings of which are shifted from each other by $\Delta Lh=\lambda(n+\frac{1}{4})$ (where $\lambda$ is the wavelength of the ultrasonic wave and "n" is an integer equal to or greater than 0) in a propagation direction of the ultrasonic wave or the reflection wave, and in which the two acoustic horn bodies are partitioned by a screen on a side of the opening and communicate with each other on a side of the transmission element or the reception element to form a common sound space.

BRIEF DESCRIPTION OF THE DRAWINGS

FIG. 4A is a graph showing a diffraction wave and a reflection wave, respectively, and FIG. 4B is a graph showing a composite wave of the diffraction wave and the reflection wave.

FIG. 9A is a graph showing a diffraction wave and a reflection wave of each path, respectively, and FIG. 9B is a graph showing a composite wave of each diffraction wave and each reflection wave.

FIGS. 10A and 10C are views each showing the volume of a diffraction wave reaching each acoustic horn body of a receiving horn from each acoustic horn body of a transmitting horn when there is a difference in the symmetry of the acoustic path formed by each acoustic horn body of the horn enclosure of FIG. 5, and FIGS. 10B and 10D are graphs showing the amplitude of each diffraction wave of FIGS. 10A and 10C, and FIG. 10E is a graph showing the amplitude of each diffraction wave of FIGS. 10A and 10C when the symmetry of an acoustic path is adjusted.

FIGS. 11A to 11E are views each showing an adjustment pattern related to the symmetry of the acoustic path of each acoustic horn body shown in FIG. 10.

FIGS. 13A to 13E are views each showing an adjustment pattern related to the symmetry of the acoustic path of each acoustic horn body shown in FIG. 12.

DESCRIPTION OF THE EMBODIMENTS

Several embodiments of the present invention will be described below with reference to the accompanying drawings.

Figure 1:
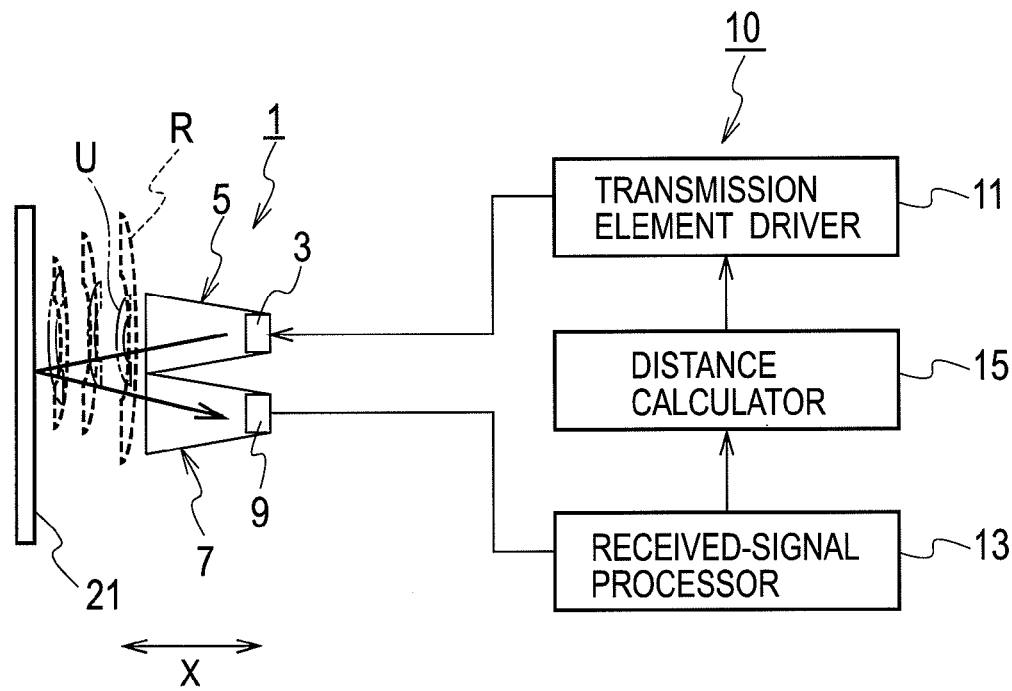
FIG. 1 is a view showing a schematic configuration of a distance measuring device of an object to be detected using an ultrasonic sensor according to one embodiment of the present invention.

FIG. 1 is a view showing the schematic configuration of a distance measuring device of an object to be detected using an ultrasonic sensor according to one embodiment of the present invention.

As shown in FIG. 1, the distance measuring device of the present embodiment includes an ultrasonic sensor 1 and a control unit 10. In the ultrasonic sensor 1, an ultrasonic wave U is emitted toward an object to be detected 21 via a transmitting horn 5 from a transmission element 3 transmitting the ultrasonic wave, and a reflection wave R from the object to be detected 21 is received by a reception element 9 via a receiving horn 7. The control unit 10 includes a transmission element driver 11 driving the transmission element 3, a received-signal processor 13 processing a received signal obtained by the receive element, and a distance calculator 15 controlling the transmission element driver 11 and the received-signal processor 13 and calculating the distance to the object to be detected 21. Note that the control unit 10 can be configured by a microcomputer and a program incorporated therein, for example.

Figure 2:
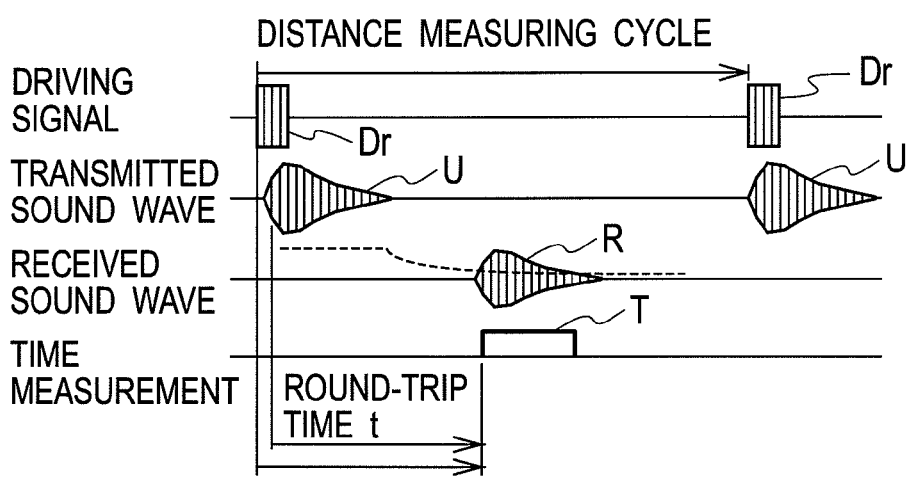
FIG. 2 is a timing chart of each signal and each sound wave generated in the distance measuring device of FIG. 1.

As shown in FIG. 2, the transmission element driver 11 outputs a driving signal Dr to the transmission element 3 for each predetermined distance measuring cycle under the control of the distance calculator 15, and the transmission element 3 driven by the driving signal Dr outputs an ultrasonic wave U. The ultrasonic wave U is reflected by the object to be detected 21 to serve a reflection wave R, which is then received by the reception element 9. The reception element 9 having received the reflection wave R outputs a received signal (not shown) to the received-signal processor 13. The received-signal processor 13 outputs a time measurement signal T to the distance calculator 15 while the received signal is being input at levels greater than a predetermined amplitude.

The distance calculator 15 calculates a time difference between when the transmission element 3 starts to output the ultrasonic wave U and when the reception element 9 starts to receive the reflection wave R (the time measurement signal T starts to be input to the distance calculator 15) as a round-trip time t from a transmission surface 31 of the transmission element 3 and a reception surface 91 of the reception element 9 (see FIG. 3) to the object to be detected 21. Then, the distance calculator 15 calculates a round trip distance by multiplying the round-trip time t by the acoustic velocity, and calculates a half value thereof as the measurement value of the distance to the object to be detected 21.

Note that the required time until the transmission element 3 outputs the ultrasonic wave U after the transmission element driver 11 outputs the driving signal Dr is held as a known value in the distance calculator 15 in advance. Accordingly, the distance calculator 15 can recognize a timing at which the transmission element 3 started to output the ultrasonic wave U, from the above-described required time and a timing at which the distance calculator 15 instructed the transmission element driver 11 to output the driving signal Dr. Moreover, the transmission surface 31 of the transmission element 3 and the reception surface 91 of the reception element 9 (see FIG. 3) are located on the same plane, and the distance calculator 15 measures the distance to the object to be detected 21, in a direction normal to this plane, in other words in a propagation direction X (see FIG. 1) of the ultrasonic wave U or the reflection wave R.

Figure 3:
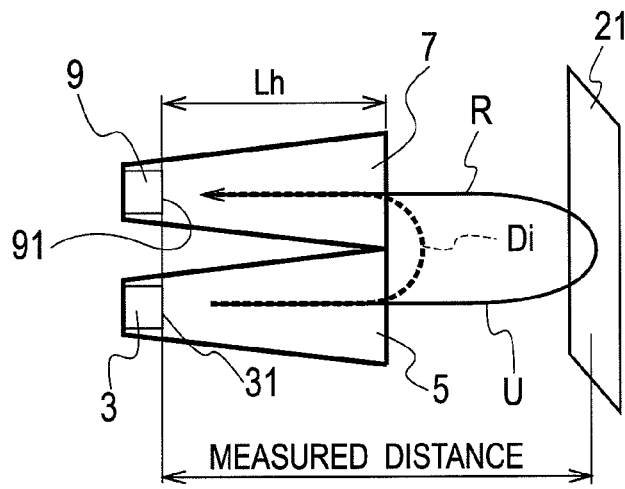
FIG. 3 is a view conceptually showing a diffraction wave generated in the ultrasonic sensor of FIG. 1.

Meanwhile, when the ultrasonic wave U, which the transmission element 3 transmitted, passes through an opening at the tip of the transmitting horn 5, as shown in FIG. 3 a part thereof is diffracted at an edge of the opening to serve as a diffraction wave Di. A part of the diffraction wave Di is again diffracted by an opening at the tip of the receiving horn 7, and travels toward the reception element 9 together with the reflection wave R from the object to be detected 21.

Figure 4A:
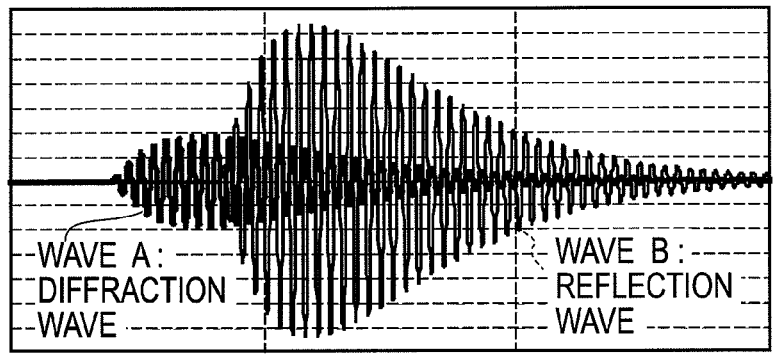
FIGS. 4A and 4B show the influence which the diffraction wave of FIG. 3 has on the detection processing of the object to be detected.
Figure 4B:
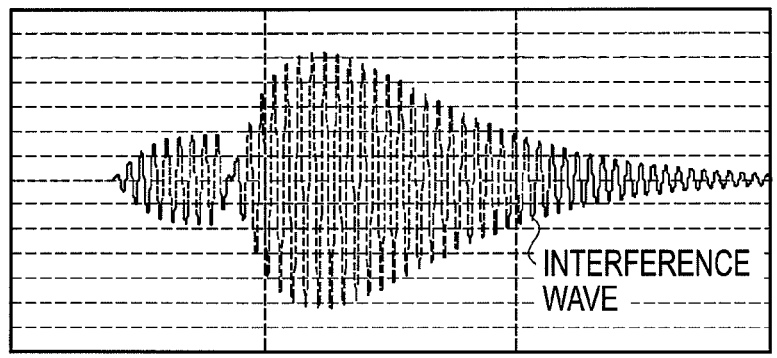

As shown in FIG. 4A, when the diffraction wave Di (wave A) is received by the reception element 9 together with the reflection wave R (wave B), the reflection wave R and the diffraction wave Di interfere with each other to serve as a composite wave (interference wave) having a waveform different from the reflection wave R, as shown in FIG. 4B. Here, because the transmission path of the reflection wave R is longer than that of the diffraction wave Di, the reflection wave R is received by the reception element 9 with a delay from the reception of the diffraction wave Di. Then, if a slice level corresponding to the amplitude of the diffraction wave Di is set to the amplitude of the composite wave which the reception element 9 receives, a leading interval that does not include the component of the reflection wave R of the composite waves can be set to a non-detection interval.

On the other hand, after the amplitude modulation of the reflection wave R by the diffraction wave Di started due to the interference between the diffraction wave Di and the reflection wave R, the amplitude of the composite wave varies depending on the phase difference between the diffraction wave Di and the reflection wave R. Therefore, a timing at which the amplitude of the composite wave exceeds the slice level is not fixed. This reduces the detection accuracy of the object to be detected 21. For this reason, conventionally, primarily methods of preventing the diffraction wave Di from being input to the reception element 9 side have been continued to be proposed.

In contrast, in the present embodiment, rather than devising a method of preventing the diffraction wave Di from being input to the reception element 9 side, we suggest actively utilizing the diffraction wave Di so that only the reflection wave R is received by the reception element 9. While the detail thereof will be clear by the description below, according to the ultrasonic sensor 1 of the present embodiment a complicated signal processing of setting the above-described slice level is not required, and a reduction in the detection accuracy of the object to be detected 21 at a short distance (in the interference region) can be suppressed.

Figure 5:
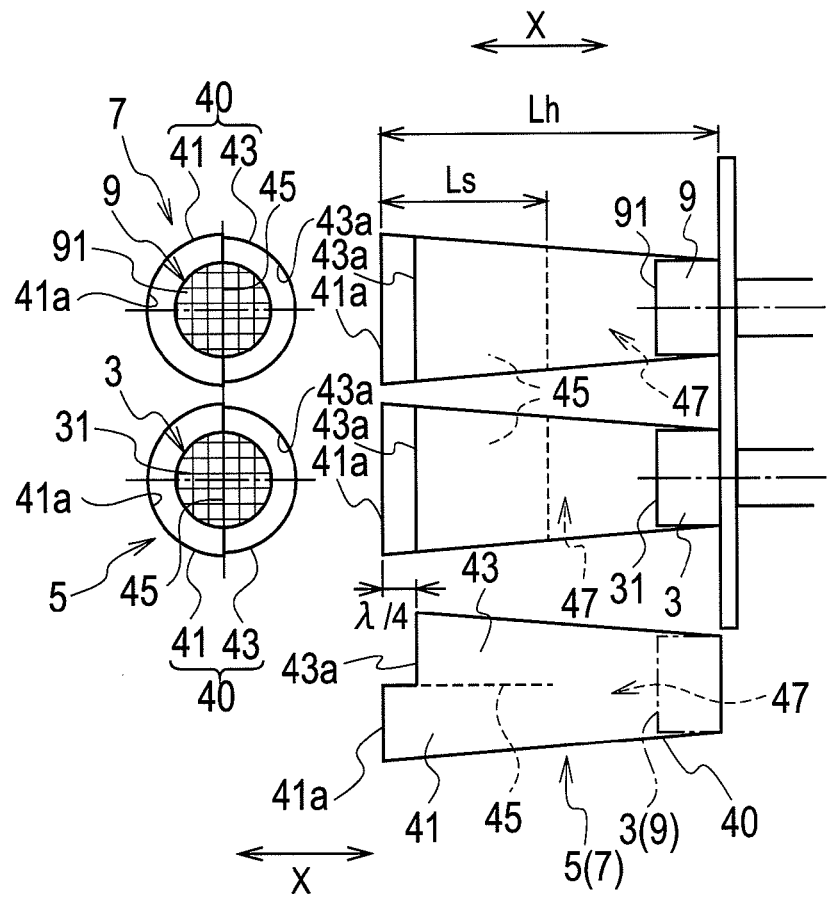
FIG. 5 is a view showing the schematic configuration of a horn enclosure configuring a transmitting horn and a receiving horn of the ultrasonic sensor of FIG. 1.

Then, in the ultrasonic sensor 1 of the present embodiment, a horn enclosure 40 of an identical shape shown in FIG. 5 is used as the transmitting horn 5 and the receiving horn 7, respectively. The horn enclosure 40 exhibits a substantially circular truncated cone shape as a whole, and includes two acoustic horn bodies 41 and 43 of a semi-circular truncated cone shape, which are formed by dividing the substantially circular truncated cone shape into two by a plane through the central axis of the horn enclosure 40. The acoustic horn bodies 41 and 43 have a dimensional difference ΔLh in the propagation direction X of the ultrasonic wave U and/or the reflection wave R. That is, in this case, if the dimension in the propagation direction X of the acoustic horn body 41 is Lh, the dimension in the propagation direction X of the acoustic horn body 43 is Lh−ΔLh. The dimensional difference ΔLh between the acoustic horn bodies 41 and 43 is set to a quarter λ/4 of the wavelength λ of the ultrasonic wave U, and the positions of the openings 41a and 43a at the tip of the acoustic horn bodies 41 and 43 shift from each other by the dimensional difference ΔLh. Note that the above-described dimensional difference ΔLh may not be a quarter (λ/4) of the wavelength λ of the ultrasonic wave U as long as the dimensions thereof satisfy ΔLh=λ(n+¼) (where "n" is an integer equal to or greater than 0).

The two acoustic horn bodies 41 and 43 are partitioned by a screen 45 on the side of the openings 41a and 43a to configure an independent acoustic path, respectively. The dimension in the propagation direction X of the screen 45 is denoted as Ls (<Lh). Moreover, the portions on the side of the transmission element 3 or the reception element 9 of the two acoustic horn bodies 41 and 43 are not partitioned by the screen 45, and communicate with each other to form a common sound space 47.

The horn enclosure 40 of the transmitting horn 5 and the horn enclosure 40 of the receiving horn 7, in the present embodiment, are attached directly or via a substrate to the transmission element 3 and the reception element 9 having a cylindrical outside shape, respectively. At this time, preferably, each horn enclosure 40 is attached so as to be able to rotate in the circumferential direction of the transmission element 3 and/or the reception element 9 so that the arrangement of the horn enclosure 40 to be described later with reference to FIGS. 10 and 11 can be adjusted. In the mounting state of FIG. 5, the screen 45 of each horn enclosure 40 is located on a straight line, and the long acoustic horn body 41 and the short acoustic horn body 43 are located on the same side across the screen 45, respectively.

Figure 6:
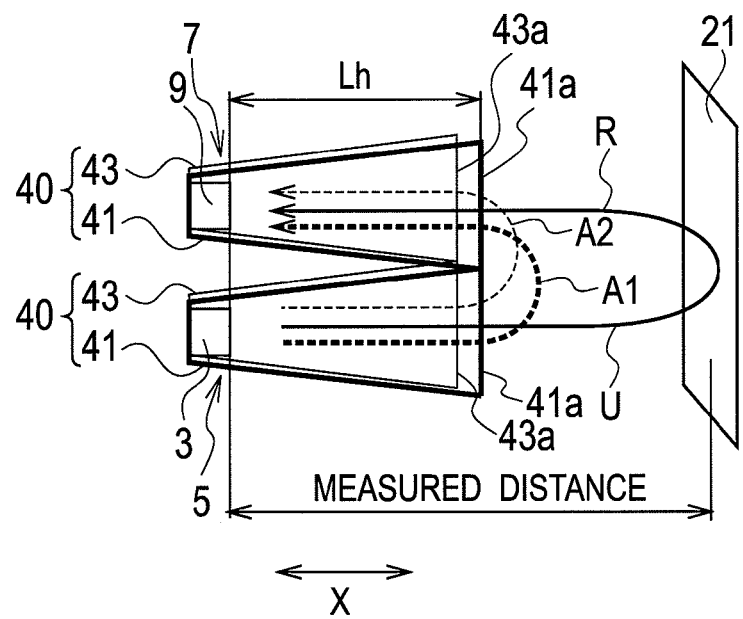
FIG. 6 is a view specifically showing paths of diffraction waves generated in the ultrasonic sensor of FIG. 1.

In the ultrasonic sensor 1 of the present embodiment, as shown in FIG. 6, when the transmission element 3 having attached thereon the horn enclosure 40 as the transmitting horn 5 transmits the ultrasonic wave U, parts thereof are diffracted by the respective openings 41a and 43a of the acoustic horn bodies 41 and 43 to serve as the diffraction waves A1 and A2. A part of each of the diffraction waves A1 and A2 is again diffracted by each of the openings 41a and 43a of the horn enclosure 40 attached to the reception element 9 as the receiving horn 7, and transmits through the inside of each of the acoustic horn bodies 41 and 43 toward the common sound space 47. Note that, in FIG. 6, although the contour of the acoustic horn body 41 and the contour of the acoustic horn body 43 are vertically shifted to each other and shown for ease of visualization of the drawing, both contours actually overlap with each other.

The diffraction waves A1 and A2 transmit through the acoustic horn bodies 41 and 43, respectively, the dimensions of which in the transmitting direction X of the openings 41a and 43a shift from each other by a quarter of the wavelength λ of the ultrasonic wave U, from the transmitting horn 5 toward the receiving horn 7. Therefore, the diffraction wave A2 results in a sound wave in opposite phase, the phase of which shifts by a half of the wavelength λ relative to the diffraction wave A1, in one round trip.

Figure 7A:
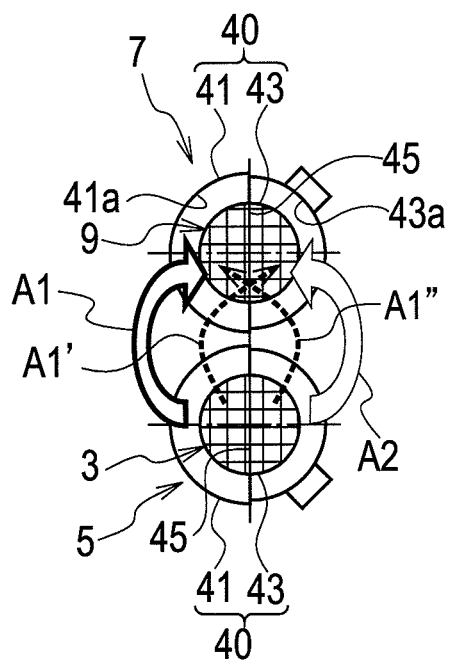
FIG. 7A is a view showing the volume of a diffraction wave reaching each acoustic horn body of a receiving horn from each acoustic horn body of the transmitting horn of FIG. 5.
Figure 8:
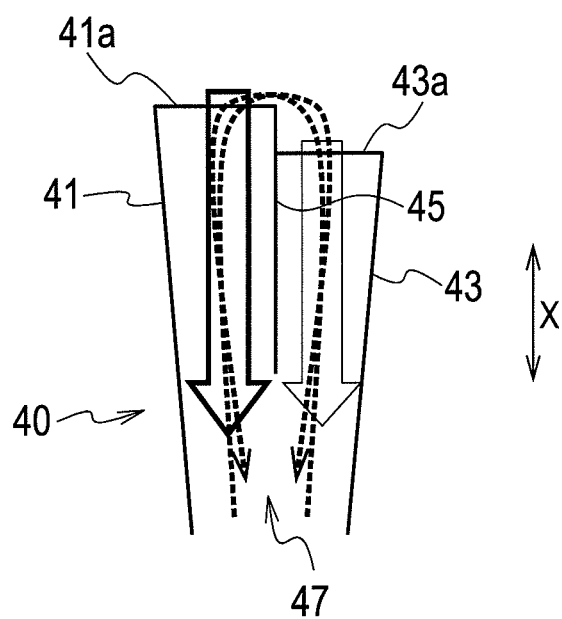
FIG. 8 is a view of the paths of some of the diffraction waves in FIG. 7.

Moreover, as shown in FIG. 7A, a part of the diffraction wave A1 diffracted by the opening 41a of the acoustic horn body 41 of the transmitting horn 5 is diffracted by the opening 43a of the acoustic horn body 43 of the receiving horn 7 to serve as a diffraction wave A1' traveling toward the common sound space 47. Similarly, a part of the diffraction wave A2 diffracted by the opening 43a of the acoustic horn body 43 of the transmitting horn 5 is diffracted by the opening 41a of the acoustic horn body 41 of the receiving horn 7 to serve as a diffraction wave A1" traveling toward the common sound space 47. These diffraction waves A1' and A1" each transmit through the acoustic horn body 41 having a longer dimension in the propagation direction X in the transmitting horn 5 or the receiving horn 7, as shown in FIG. 8, and therefore have the same phase as that of the diffraction wave A1 transmitting through the acoustic horn body 41, in both the transmitting horn 5 and the receiving horn 7. For this reason, the diffraction waves A1' and A1" can be handled together with the diffraction wave A1 in terms of phase.

Then, in the ultrasonic sensor 1 of the present embodiment, the diffraction wave A1 (and the diffraction waves A1' and A1") and the diffraction wave A2, in mutually opposite phases, diffracting from the enclosure 40 of the transmitting horn 5 to the horn enclosure 40 of the receiving horn 7 are caused to interfere with each other by the common sound space 47 of the horn enclosure 40 of the receiving horn 7 so as to be attenuated or cancelled out.

Here, for simplification of the explanation, without considering the presence of the diffraction waves A1' and A1" in FIG. 7A, and limiting only to the diffraction waves A1 and A2, a relationship between the arrangement of the horn enclosure 40 of the transmitting horn 5 and the horn enclosure 40 of the receiving horn 7 and the diffraction wave is described. When an effective acoustic path from the acoustic horn body 41 of the transmitting horn 5 to the acoustic horn body 41 of the receiving horn 7 and an effective acoustic path from the acoustic horn body 43 of the transmitting horn 5 to the acoustic horn body 43 of the receiving horn 7 are symmetric to each other, the volumes (amplitudes) of the diffraction wave A1 and the diffraction wave A2 are equal.

Figure 7B:
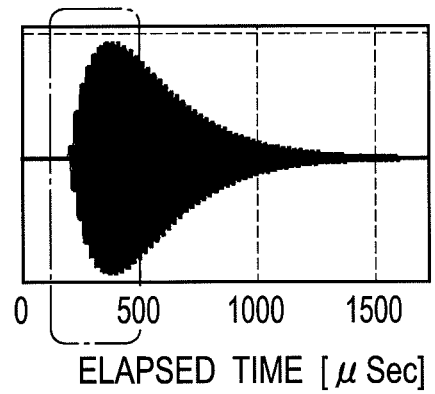
FIG. 7B is a graph showing a relationship between the amplitude of each diffraction wave and the elapsed time when the path is simplified.

In this case, as shown in FIG. 7A, the horn enclosure 40 of the transmitting horn 5 and the horn enclosure 40 of the receiving horn 7 are arranged so that the area of a region, where the opening 41a of the acoustic horn body 41 of the transmitting horn 5 and the opening 41a of the acoustic horn body 41 of the receiving horn 7 face to each other, becomes equal to the area of a region, where the opening 43a of the acoustic horn body 43 on the transmitting side and the opening 43a of the acoustic horn body 43 on the receiving side face to each other, so that the diffraction wave A1 and the diffraction wave A2 with the same amplitude can be obtained as shown in FIG. 7B. To put it another way, the horn enclosure 40 of the transmitting horn 5 and the horn enclosure 40 of the receiving horn 7 are arranged so that the screen 45 of the horn enclosure 40 of the transmitting horn 5 and the screen 45 of the horn enclosure 40 of the receiving horn 7 are located on a straight line.

Figure 9A:
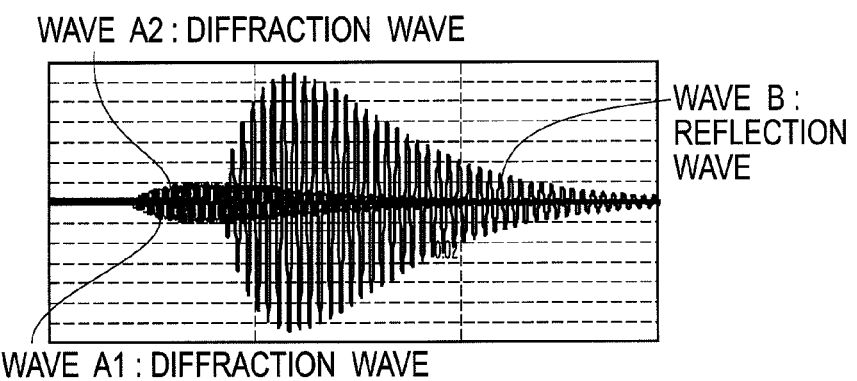
FIGS. 9A and 9B specifically show the influence which the diffraction wave of each path of FIG. 7 has on the detection processing of an object to be detected.
Figure 9B:
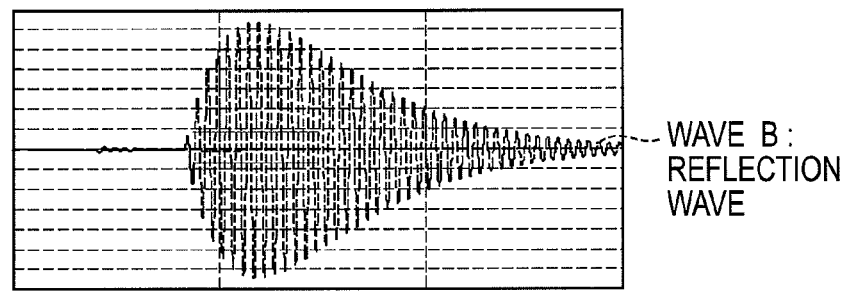

If the diffraction wave A1 and the diffraction wave A2 with the same amplitude are obtained, then as shown in FIG. 9A, the diffraction wave A1 and the diffraction wave A2 in opposite phase having reached the common sound space 47 of the horn enclosure 40 of the receiving horn 7 interfere with each other, so that both diffraction waves A1 and A2 can be canceled out as shown in FIG. 9B. Thus, only with the reflection wave R (wave B) reaching the reception element 9, the distance calculator 15 can properly measure the distance to the object to be detected 21 based on the time measurement signal T from the received-signal processor 13.

In contrast, as shown hi FIGS. 10A and 10C, when an effective acoustic path from the acoustic horn body 41 of the transmitting horn 5 to the acoustic horn body 41 of the receiving horn 7 and an effective acoustic path from the acoustic horn body 43 of the transmitting horn 5 to the acoustic horn body 43 of the receiving horn 7 are asymmetric to each other, the volumes (amplitudes) of the diffraction wave A1 and the diffraction wave A2 differ from each other. This has two cases: "the volume of the diffraction wave A1>the volume diffraction wave A2"; and "the volume of the diffraction wave A1<the volume of the diffraction wave A2".

When "the volume of the diffraction wave A1>the volume diffraction wave A2", the amplitude of the diffraction wave A1 becomes larger than the amplitude of the diffraction wave A2 as shown in FIG. 10B. In this case, as shown in FIG. 10A, the arrangement of each horn enclosure 40 on the transmitting side and on the receiving side is adjusted so that the area of a region, where the opening 43a of the acoustic horn body 43 on the transmitting side and the opening 43a of the acoustic horn body 43 on the receiving side face to each other becomes larger than the area of a region, where the opening 41a of the acoustic horn body 41 on the transmitting side and the opening 41a of the acoustic horn body 41 on the receiving side face to each other.

Moreover, when "the volume of the diffraction wave A1<the volume of the diffraction wave A2", the amplitude of the diffraction wave A2 becomes larger than the amplitude of the diffraction wave A1 as shown in FIG. 10D. In this case, as shown in FIG. 10C, the arrangement of each horn enclosure 40 of the transmitting horn 5 and the receiving horn 7 is adjusted so that the area of a region, where the opening 41a of the acoustic horn body 41 of the transmitting horn 5 and the opening 41a of the acoustic horn body 41 of the receiving horn 7 face to each other, becomes larger than the area of a region, where the opening 43a of the acoustic horn body 43 of the transmitting horn 5 and the opening 43a of the acoustic horn body 43 of the receiving horn 7 face to each other. To put it another way, each horn enclosure 40 of the transmitting horn 5 and the receiving horn 7 is arranged so that an angle θ formed by the screen 45 of the horn enclosure 40 of the transmitting horn 5 and the screen 45 of the horn enclosure 40 of the receiving horn 7 becomes a superior angle ($\pi<\theta<2\pi$) on the side of the acoustic horn body 41 of the transmitting horn 5 and on the side of the acoustic horn body 41 of the receiving horn 7.

If the arrangement of each horn enclosure 40 of the transmitting horn 5 and the receiving horn 7 is adjusted as described above, the diffraction wave A1 and the diffraction wave A2 with the same amplitude can be obtained as shown in FIG. 10E. Thus, the diffraction wave A1 and the diffraction wave A2 can be canceled out by the common sound space 47 of the horn enclosure 40 on the receiving side, and only the reflection wave R can be caused to reach the reception element 9, thereby allowing the distance calculator 15 of FIG. 1 to properly measure the distance to the object to be detected 21.

Note that, from the view point of reliably achieving the canceling-out due to the interference of the diffraction waves A1 and A2 in opposite phase in the common sound space 47, the dimension (Lh-Ls: see FIG. 5) of the common sound space 47 in the propagation direction X is preferably set to be equal to or greater than a half wavelength $\lambda/2$ of the ultrasonic wave U or the reflection wave R.

In the above description, for convenience of explanation, the presence of the diffraction waves A1' and A1" have not been taken into consideration, but actually the volume of the diffraction wave A1 will increase by the volumes of these diffraction waves A1' and A1", and therefore the arrangement of each horn enclosure 40 on the transmitting side and on the receiving side needs to be determined or adjusted taking into consideration the actual increase in the amplitude of the diffraction wave A1 due to these volumes.

Note that there are several patterns in adjusting the arrangement of each horn enclosure 40 of the transmitting horn 5 and the receiving horn 7. For example, when the arrangement of each horn enclosure 40 of the transmitting horn 5 and the receiving horn 7 is adjusted from a default arrangement, in which the screen 45 of the horn enclosure 40 of the transmitting horn 5 and the screen 45 of the horn enclosure 40 of the receiving horn 7 are located on a straight line as shown in FIG. 11A, there are a pattern in which only one of the hone enclosures 40 is rotated and adjusted as shown in FIGS. 11B and 11C, and a pattern in which both horn enclosures 40 are rotated and adjusted as shown in FIGS. 11D and 11E.

By appropriately performing such an adjustment, the amplitude of the diffraction wave A1 and the amplitude of the diffraction wave A2 (including the amplitudes of the diffraction waves A1' and A1") may be matched with each other.

As described above, according to the ultrasonic sensor 1 of the present embodiment, as the horn enclosure of the transmitting horn 5 or the receiving horn 7, the horn enclosure 40 with two acoustic horn bodies 41 and 43 having the dimensional difference ΔLh of a quarter $\lambda/4$ of the wavelength λ of the ultrasonic wave U in the propagation direction X of the ultrasonic wave U or the reflection wave R is used. Then, the amplitude of the diffraction wave A1 and the amplitude of the diffraction wave A2 (including the amplitudes of the diffraction waves A1' and A1") in opposite phase between the transmitting horn 5 and the receiving horn 7 are caused to match with each other, thereby canceling out the both diffraction waves A1 and A2 in the common sound space 47 of the horn enclosure 40, which is not partitioned for each of the acoustic horn bodies 41 and 43 by the screen 45, on the front of the reception element 9.

Therefore, there is no need to provide a spacing between the opening of the transmitting horn 5 and the opening of the receiving horn 7 (i.e., between the openings 41a and 43a of the acoustic horn bodies 41 and 43 of each horn enclosure 40 of the transmitting horn 5 and the receiving horn 7). Accordingly, a reduction in the detection accuracy of the distance to the object to be detected 21 or the like due to the influence of the diffraction waves A1 and A2 (including the diffraction waves A1' and A1") can be suppressed without spacing apart the transmitting horn 5 and the receiving horn 7. That is, the distance to the object to be detected 21 at a short distance or the presence or absence of the object to be detected 21 can be accurately detected without increasing the shortest detection range.

Figure 12:
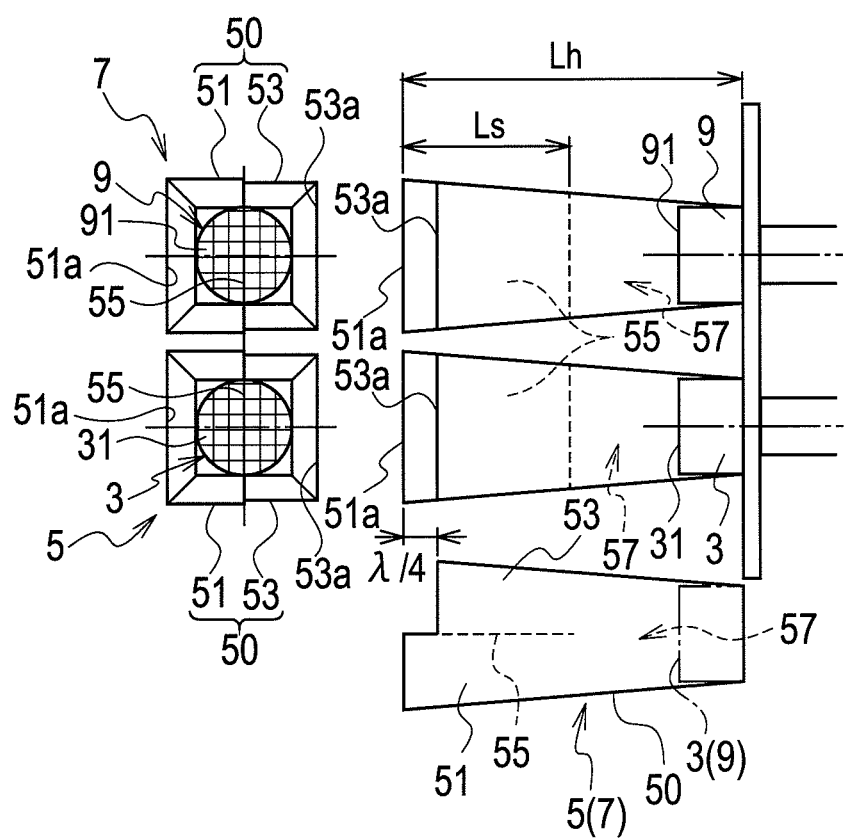
FIG. 12 is a view showing the schematic configuration of another example of the horn enclosure configuring the transmitting horn and the receiving horn of the ultrasonic sensor of FIG. 1.

Note that, in the embodiment described above, the horn enclosure 40 exhibiting a substantially circular truncated cone shape as a whole has been taken as an example and described, but a horn enclosure with other shape, such as a substantially polygonal pyramid shape, may be employed. For example, as shown in FIG. 12, the horn enclosure 50 may be configured by two acoustic horn bodies 51 and 53 having a rectangular cross section, which are formed by dividing a horn enclosure 50 of a square pyramid shape into two by a plane extending in the direction of the central axis of the horn enclosure 50. In this case, the acoustic horn bodies 51 and 53 have the dimensional difference ΔLh of a quarter $\lambda/4$ of the wavelength λ of the ultrasonic wave U in the propagation direction X of the ultrasonic wave U or the reflection wave R, and the positions of openings 51a and 53a at the tip of both the acoustic horn bodies 51 and 53 shift from each other by the dimensional difference ΔLh. It should be noted that the dimensional difference ΔLh between the acoustic horn bodies 51 and 53, as with the case of the acoustic horn bodies 41 and 43, may not be a quarter ($\lambda/4$) of the wavelength λ of the ultrasonic wave U as long as the dimensions thereof satisfy ΔLh=$\lambda$(n+¼) (where "n" is an integer equal to or greater than 0).

Moreover, the two acoustic horn bodies 51 and 53 are partitioned by a screen 55 for each of the acoustic horn bodies 51 and 53 on the sides of the openings 51a and 53a to configure an independent acoustic path, respectively. Furthermore, the portions on the side of the transmission element 3 or the reception element 9 of the two acoustic horn bodies 51 and 53 are not partitioned by the screen 55, and communicate with each other to form a common sound space 57.

Also with regard to the common sound space 57, from a view point of reliably achieving the canceling-out due to the interference of the diffraction waves in opposite phase (e.g., the interference between the diffraction wave A1 and the diffraction wave A2 (including the diffraction waves A' and A1")), the dimension (Lh−Ls: see FIG. 12) of the common sound space 57 in the propagation direction X is preferably set to be equal to or greater than a half wavelength λ/2 of the ultrasonic wave U or the reflection wave R.

Even with the horn enclosure 50 with such a shape, the same effect as the effect which the horn enclosure 40 of the above-described embodiment exhibits can be obtained. Note that, when an effective acoustic path of the acoustic horn body 51 from the transmitting horn 5 to the receiving horn 7 and an effective acoustic path of the acoustic horn body 53 from the transmitting horn 5 to the receiving horn 7 are not symmetric to each other, the arrangement of each horn enclosure 50 of the transmitting horn 5 and the receiving horn 7 relative to the transmission element 3 or the reception element 9 may be adjusted.

For example, when the arrangement of each horn enclosure 50 of the transmitting horn 5 and the receiving horn 7 is adjusted from a default arrangement in which the both screens 55 are located on a straight line as shown in FIG. 13A, only one horn enclosure 50 can be deformed so as to have a parallelogram-shaped cross section for adjustment as shown in FIGS. 11B and 11C, or both the horn enclosures 50 can be deformed so as to each have a parallelogram-shaped cross section for adjustment as shown in FIGS. 11D and 11E.

Note that, if the horn enclosures 40 and 50 of the transmitting horn 5 and the receiving horn 7 are attached to the transmission element 3 or the reception element 9, respectively, in advance so that an effective acoustic path of the acoustic horn bodies 41 and 51 from the transmitting horn 5 to the receiving horn 7 and an effective acoustic path of the acoustic horn bodies 43 and 53 from the transmitting horn 5 to the receiving horn 7 become symmetric to each other and furthermore this state can be maintained thereafter, then the configuration for adjusting the arrangement of the horn enclosures 40 and 50 relative to the transmission element 3 or the reception element 9 may be omitted.

Moreover, if the diffraction waves A1 and A2 (including the diffraction waves A1' and A1") in opposite phase can be attenuated to below an allowable range by the interference, the dimensions of the common sound spaces 47 and 57 in the propagation direction X may be set to be less than a half wavelength (λ/2) of the ultrasonic wave U or the reflection wave R.

As described above, according to the ultrasonic sensor of the above-described embodiment, an ultrasonic wave transmitted from a transmission element propagates in two acoustic horn bodies, respectively, through a common sound space of a horn enclosure of a transmitting horn, and the resulting ultrasonic waves are transmitted from each opening, which shifts by λ(n+¼) (where "n" is an integer equal to or greater than 0) in the propagation direction, toward an object to be detected, respectively. Then, a part of the ultrasonic wave is diffracted by the opening of each acoustic horn body to serve as a diffraction wave. The diffraction wave generated at the opening of each acoustic horn body of the transmitting horn is diffracted by the opening of each acoustic horn body of the receiving horn, and propagates toward the common sound space of the receiving horn.

Accordingly, a propagation distance of the diffraction wave, which is generated at the opening of the acoustic horn body with a short dimension of the transmitting horn and is diffracted by the opening of the acoustic horn body with a short dimension of the receiving horn and travels toward the common sound space, is shorter by 2λ(n+¼) than a propagation distance of the diffraction wave having traveled through other paths. Here, the other paths refer to a path from an acoustic horn body with a short dimension of the transmitting horn through an acoustic horn body with a long dimension of the receiving horn, a path from an acoustic horn body with a long dimension of the transmitting horn through an acoustic horn body with a short dimension of the receiving horn, and a path from an acoustic horn body with a long dimension of the transmitting horn through an acoustic horn body with a long dimension of the receiving horn.

In this manner, two diffraction waves, the propagation distances of which differ from each other by 2λ(n+¼), result in sound waves in opposite phase, the phases of which differ from each other by a half wavelength, and therefore upon reaching the common sound space of the horn enclosure of the receiving horn, the two diffraction waves will attenuate due to the interference. Accordingly, before the diffraction wave generated at the opening of the transmitting horn is received by the reception element, it can be attenuated in sound pressure in the common sound space of the receiving horn, thereby suppressing a reduction in the detection accuracy of an object to be detected. In particular, the diffraction wave with each propagation distance is caused to have a nearly equal amplitude, so that the diffraction waves can be cancelled out and a reduction in the detection accuracy of an object to be detected can be prevented.

Then, by configuring the horn enclosures of the transmitting horn and the receiving horn with two acoustic horn bodies, the positions of the openings of which differ, the diffraction waves in opposite phase each having a different propagation distance are generated and attenuated, and therefore there is no need to provide a spacing between the openings of the transmitting horn and the receiving horn. For this reason, a reduction in the detection accuracy due to the influence of a diffraction wave can be suppressed without spacing apart both the transmitting horn and the receiving horn, and the distance to an object to be detected at a short distance or the presence or absence of an object to be detected can be accurately detected without increasing the shortest detection range.

Moreover, according to the ultrasonic sensor of the above-described embodiment, if at least one of the position of the screen of a transmitting horn relative to a transmission element and the position of the screen of the receiving horn relative to a reception element is varied in the plane perpendicular to the propagation direction of an ultrasonic wave or a reflection wave, the area of a region where the opening of each acoustic horn body of the transmitting horn and the opening of each acoustic horn of the receiving horn face to each other, will vary. Then, the volume of a diffraction wave reaching the opening of each acoustic horn of the receiving horn from the opening of each acoustic horn body of the transmitting horn will vary and the amplitude of each diffraction wave reaching the common sound space of the receiving horn in opposite phase will vary.

Accordingly, an environment can be easily realized, where the amplitude of each diffraction wave reaching the common sound space of the receiving horn in opposite phase can be matched with each other so as to cancel out the both diffraction waves when these diffraction waves interfere with each other in the common sound space.

Furthermore, the common sound space in the ultrasonic sensor of the above-described embodiment has a dimension equal to or greater than λ/2 in the propagation direction, and therefore a space capacity for two diffraction waves, which have reached the common sound space of the receiving horn in opposite phase, to sufficiently interfere with each other can be secured.

The present application claims the benefit of priority under 35 U.S.C. §119 to Japanese Patent Application No. 2011-231587, filed on Oct. 21, 2011, the entire content of which is incorporated herein by reference.

What is claimed is:

1. An ultrasonic sensor, comprising:
a transmitting horn configured to transmit an ultrasonic wave generated by a transmission element; and
a receiving horn configured to cause a reception element to receive a reflection wave from an object detected by the transmitted ultrasonic wave, wherein
the transmitting horn and the receiving horn each include a horn enclosure,
each horn enclosure comprises two acoustic horn bodies and a screen,
each acoustic horn body has an opening and the openings of the acoustic horn bodies are shifted from each other by $\Delta Lh = \lambda(n+¼)$, where $\Delta Lh$ is a dimensional difference in a propagation direction of the ultrasonic wave, $\lambda$ is the wavelength of the ultrasonic wave and "n" is an integer one of equal to 0 and greater than 0,
the two acoustic horn bodies of each horn enclosure are partitioned by the screen of each horn enclosure on a side of each of the openings of the horn bodies, and
the screen of each horn enclosure is configured to provide a common sound space in the respective horn enclosure at a side of one of the transmission element and the reception element to allow the two acoustic horn bodies of the associated horn enclosure to communicate with each other at the common sound space.

2. The ultrasonic sensor according to claim 1, wherein each horn enclosure is configured in such a way that a position of the respective screen relative to at least one of the transmission element and the reception element can be varied in a plane perpendicular to the propagation direction.

3. The ultrasonic sensor according to claim 1, wherein the common sound space has a dimension one of equal to and greater than $\lambda/2$ in the propagation direction.

* * * * *